US012478416B2

(12) United States Patent
Toavs

(10) Patent No.: US 12,478,416 B2
(45) Date of Patent: Nov. 25, 2025

(54) TRACTION TENSIONING APPARATUS AND SYSTEM

(71) Applicant: Bennett Toavs, St. Paul, MN (US)

(72) Inventor: Bennett Toavs, St. Paul, MN (US)

( * ) Notice: Subject to any disclaimer, the term of this patent is extended or adjusted under 35 U.S.C. 154(b) by 1069 days.

(21) Appl. No.: 17/494,054

(22) Filed: Oct. 5, 2021

(65) Prior Publication Data

US 2022/0104860 A1 Apr. 7, 2022

Related U.S. Application Data

(60) Provisional application No. 63/088,986, filed on Oct. 7, 2020.

(51) Int. Cl.
*A61B 17/88* (2006.01)
*A61B 17/64* (2006.01)

(52) U.S. Cl.
CPC ...... *A61B 17/8869* (2013.01); *A61B 17/6408* (2013.01); *A61B 17/8861* (2013.01)

(58) Field of Classification Search
CPC ............ A61B 17/8869; A61B 17/6408; A61B 17/8861; A61F 5/04; A61H 1/02; A61H 1/0218; A61H 1/0222; A61H 1/0237
USPC ....................................................... 602/32, 33
See application file for complete search history.

(56) References Cited

U.S. PATENT DOCUMENTS

| | | | | |
|---|---|---|---|---|
| 2,655,668 | A * | 10/1953 | Nelson | A61G 7/0501 5/651 |
| 3,167,068 | A * | 1/1965 | Carr | A61H 1/0218 602/32 |
| 3,795,243 | A * | 3/1974 | Miller | A61F 5/055 297/393 |
| 4,664,099 | A * | 5/1987 | Pearl, Jr. | A61F 5/04 602/33 |
| 4,712,770 | A | 12/1987 | Wiederkehr | |
| 5,312,410 | A | 5/1994 | Miller | |
| 5,395,374 | A | 3/1995 | Miller | |
| 6,245,034 | B1 | 6/2001 | Bennett | |
| 6,595,994 | B2 | 7/2003 | Kilpela | |
| 8,469,966 | B2 | 6/2013 | Allen | |
| 9,408,637 | B2 | 8/2016 | Mikhail | |
| 2006/0015105 | A1 | 1/2006 | Warren | |
| 2006/0264945 | A1 | 11/2006 | Sweeney, II | |
| 2006/0282033 | A1 * | 12/2006 | Zeide | A61F 5/373 602/20 |
| 2020/0178947 | A1 | 6/2020 | Corrao | |

* cited by examiner

*Primary Examiner* — Caitlin A Carreiro

(57) ABSTRACT

A traction tensioning apparatus includes a housing that has a first end and a second end. An anchor point is mounted to the housing and is attachable to a first tether that is in-line with a traction system and extending away from the housing in a first direction. An urging assembly is engaged with the anchor point. The urging assembly is tension actuated to urge the anchor point toward the second end and releasably actuated to allow the anchor point to move toward the first end. An attachment point is mounted to the housing and is attachable to a second tether in-line with the traction system and extending away from the housing in a second direction. The attachment point is movable in the first and second directions relative to the housing. A biasing member is engaged with the attachment point and biases the attachment point in the first direction.

7 Claims, 12 Drawing Sheets

TRACTION TENSIONING APPARATUS AND SYSTEM

CROSS-REFERENCE TO RELATED APPLICATIONS

I hereby claim the benefit under 35 U.S.C. Section 119(e) of U.S. Provisional Application 63/088,986 filed on Oct. 7, 2020.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to traction device and more particularly pertains to a new traction device for applying a selectable and consistent amount of tension on a traction line. The amount of tension can be increased in small increments until the required amount is obtained and then thereafter maintained in a stable condition. Moreover, the apparatus described herein allows for easier transfer of patients between a bed and a wheelchair as well as providing a safer and more effective traction system for use in the field by emergency personnel.

(2) Description of Related Art Including Information Disclosed Under 37 CFR 1.97 and 1.98

The prior art relates to traction devices that are used to exert tension on selected points of leg, particularly after traumatic femoral fracture injuries. These devices are typically characterized by pulleys, pulley lines, and weights attached to the pulley lines. While these device are effective for their specific usage, the weights and pulleys do not allow for easy movement of the patient in and out of bed and cannot be used in the field during an emergency situation. Moreover, changing the weights themselves can difficult.

BRIEF SUMMARY OF THE INVENTION

An embodiment of the disclosure meets the needs presented above by generally comprising a housing that has a first end, a second end and a perimeter wall extending between the first and second ends. An anchor point is mounted to the housing and is attachable to a first tether is in-line with a traction system and extending away from the housing in a first direction. An urging assembly is engaged with the anchor point. The urging assembly is tension actuated to urge the anchor point toward the second end and releasably actuated to allow the anchor point to move toward the first end. An attachment point is mounted to the housing and is attachable to a second tether in-line with the traction system and extending away from the housing in a second direction. The attachment point is movable in the first and second directions relative to the housing. A biasing member is engaged with the attachment point and biases the attachment point in the first direction.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
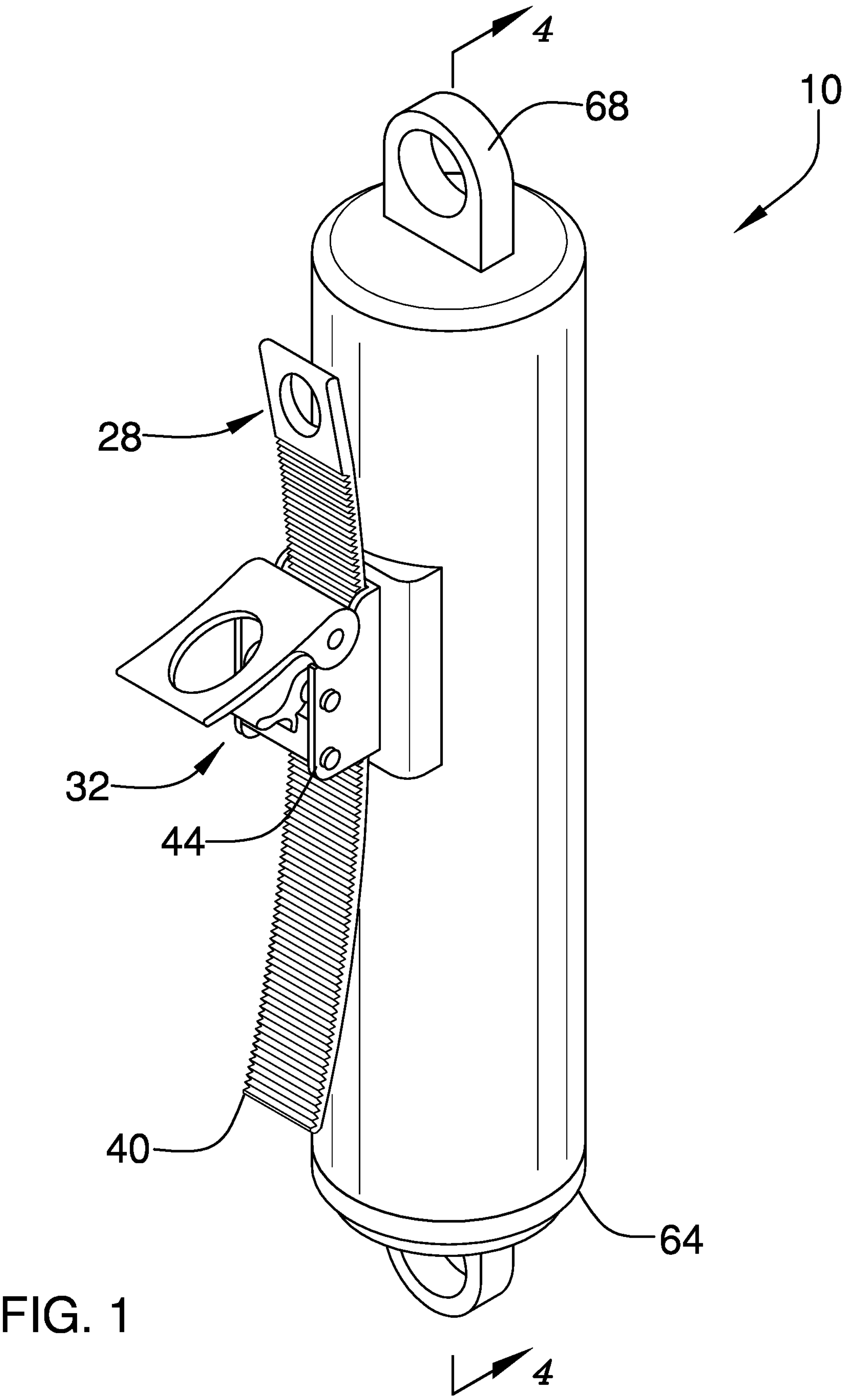
FIG. 1 is a top and side isometric view of a traction tensioning apparatus and system according to an embodiment of the disclosure.

With reference now to the drawings, and in particular to FIGS. 1 through 12 thereof, a new traction device embodying the principles and concepts of an embodiment of the disclosure and generally designated by the reference numeral 10 will be described.

As best illustrated in FIGS. 1 through 12, the traction tensioning apparatus 10 and system 12 generally comprises an intermediary implement used within a traction system 12 to provide a selected amount of pulling tension on portions of a person's leg 14, such as when they have suffered a traumatic femoral fracture and during orthopedic traction.

To this end, the apparatus 10 includes a housing 20 having a first end 22, a second end 24, and a perimeter wall 26 extending between the first 22 and second 24 ends. As can be seen in the Figures, the housing 20 may be provided with a cylindrical shape.

An anchor point 28 is mounted to the housing 20 and is configured to be attached to a first tether 30 that is in-line with the traction system 12 and extends away from the housing 20 in a first direction. The term "in-line" used herein defines elements upon which tension is affected when a traction system 12 is being used and which typically are positioned between a fixed point and a person's leg 14 on which traction is being use. The anchor point 28 may include structures that allow for releasably coupling to the first tether 30 such as a closed loop, a hook, or an openable loop for engagement. Alternatively, the anchor point 28 may comprise the point where the first tether 30 is non-removably coupled to the apparatus 10.

An urging assembly 32 is engaged with the anchor point 28. The urging assembly 32 is tension actuated to urge the anchor point 28 toward the second end 24 and, alternatingly, releasably actuated to allow the anchor point 28 to move toward the first end 22. An attachment point 34 is mounted to the housing 20 and is configured to be attached to a second tether 36 that is also in-line with the traction system 12 and extends away from the housing 20 in a second direction. The attachment point 34 is movable in the first and second directions relative to the housing 20. Typically, the attachment point 34 includes a closed loop, a hook, or an openable loop for engagement with the second tether. A biasing member 38 is engaged with the attachment point 34 and biases the attachment point 34 in the first direction.

It should therefore be understood that as greater tension is placed on the first 30 and second 36 tethers, the attachment point 34 is moved in the second direction relative to the housing 20. That is, because the first 30 and second 36 tethers are attached to what are, essentially, fixed points, the housing 20 moves in the first direction toward a person's leg 14 to simultaneously cause the attachment point 34 to be pulled in the second direction away from the housing 20. As the attachment point moves in the second direction, the force exerted on the first 30 and second 36 tethers by the biasing member 38 increases. The tension, therefore, can be increased with tension actuation and lowered or eliminated with release actuation.

In one embodiment, shown in FIG. 1, the urging assembly 32 includes a strap 40 that is attached to the anchor point 28. The anchor point 28, in this embodiment, is integral with the strap 40. The strap 40 includes a plurality of teeth 42 and a ratchet mechanism 44 is engaged with the strap 40. The ratchet mechanism 44 is tension actuated to pull the anchor point 28 in the second direction. In this embodiment, the urging assembly 32 may be of the type conventionally used in the skiing and snowboarding industries to close and tighten bindings on a person's foot or footwear. Examples of such devices are found in U.S. Pat. Nos. 5,416,952, 6,669,211, 8,337,369, and 6,748,630 all incorporated herein by reference. These devices typically at least include a tension lever 46 to pull the strap 40 tighter through a lock 48 and a release lever 50 or switch to release the lock 48. It should be understood that other urging assemblies 32 may be utilized such a combination ratchet and fabric like strap as found in U.S. Pat. No. 5,927,744 or cables on a winding mechanisms such as taught by U.S. Pat. No. 7,992,261 each incorporated by reference. Turnbuckle type couplers may also be utilized as an urging assembly 32.

The attachment point 34 of this embodiment includes a rod 52 slidably extending through the second end 24 of the housing 20. The rod 52 has an internal end 54 positioned within the housing 20 and an external end 56 positioned external of the housing 20 wherein the second tether 36 is attachable to rod 52 adjacent to the external end 56. The second tether 36 may be removably or non-removably attached to the rod 52. A head 58 is mounted on the rod 52 and may be configured to threadably receive the internal end 54. The first end 22 of the housing 20 may be removably attached to the perimeter wall 26 to facilitate access to the head 58. This will allow adjustment of a position of the head 58 relative to the external end 56 of the rod 52 for reasons which will become clear below.

Figure 2:
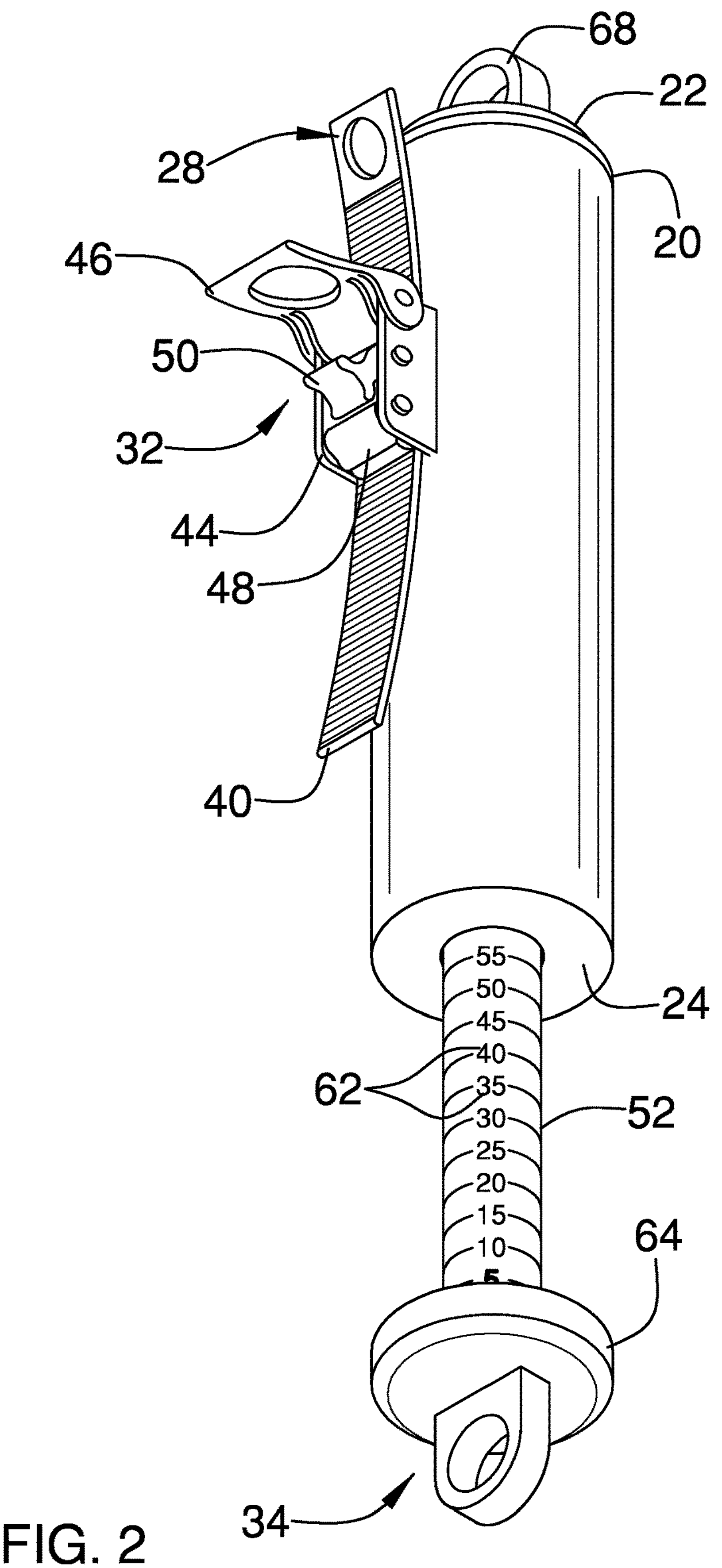
FIG. 2 is a bottom and side isometric view of an embodiment of the disclosure.
Figure 3:
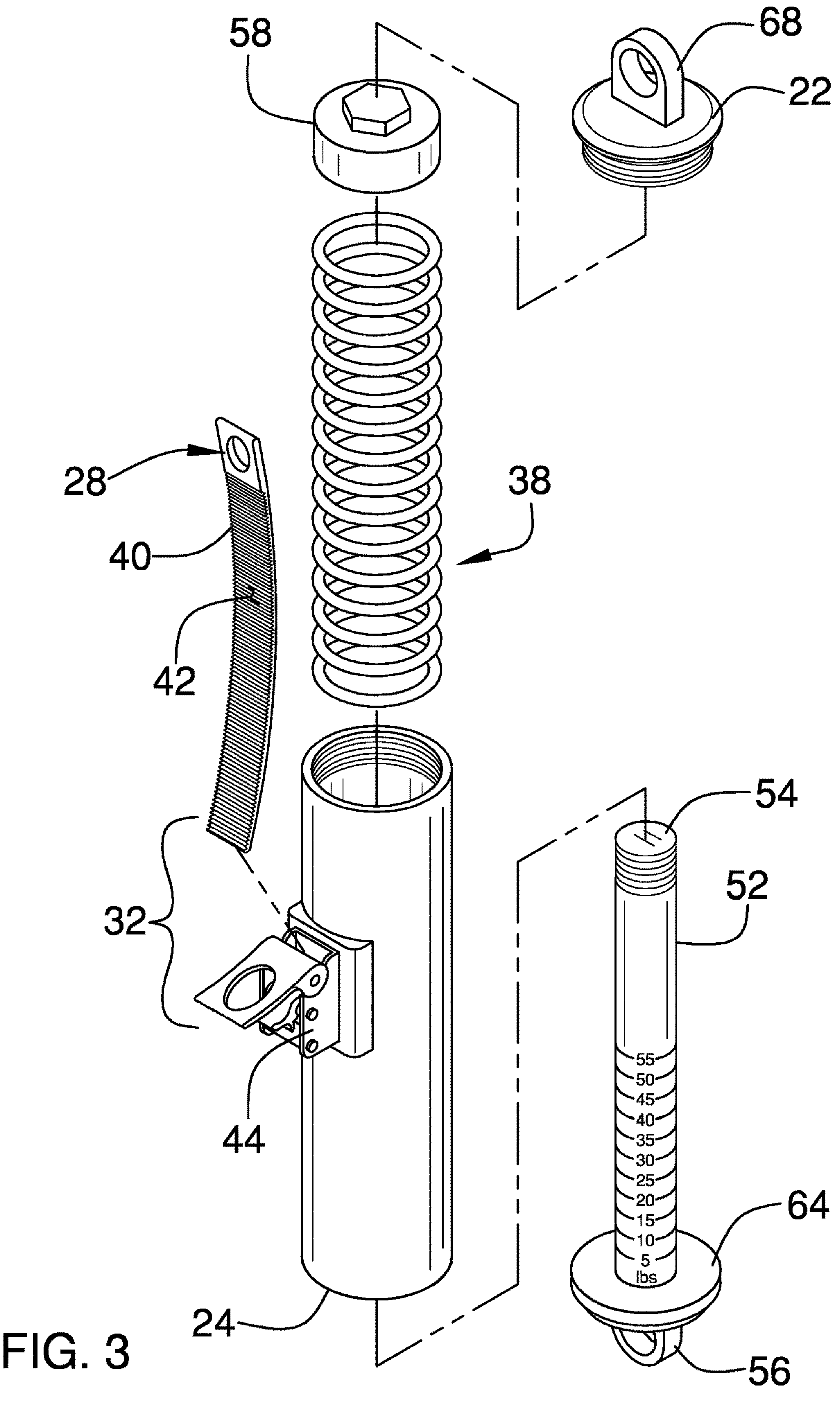
FIG. 3 is an exploded isometric view of an embodiment of the disclosure.
Figure 4:
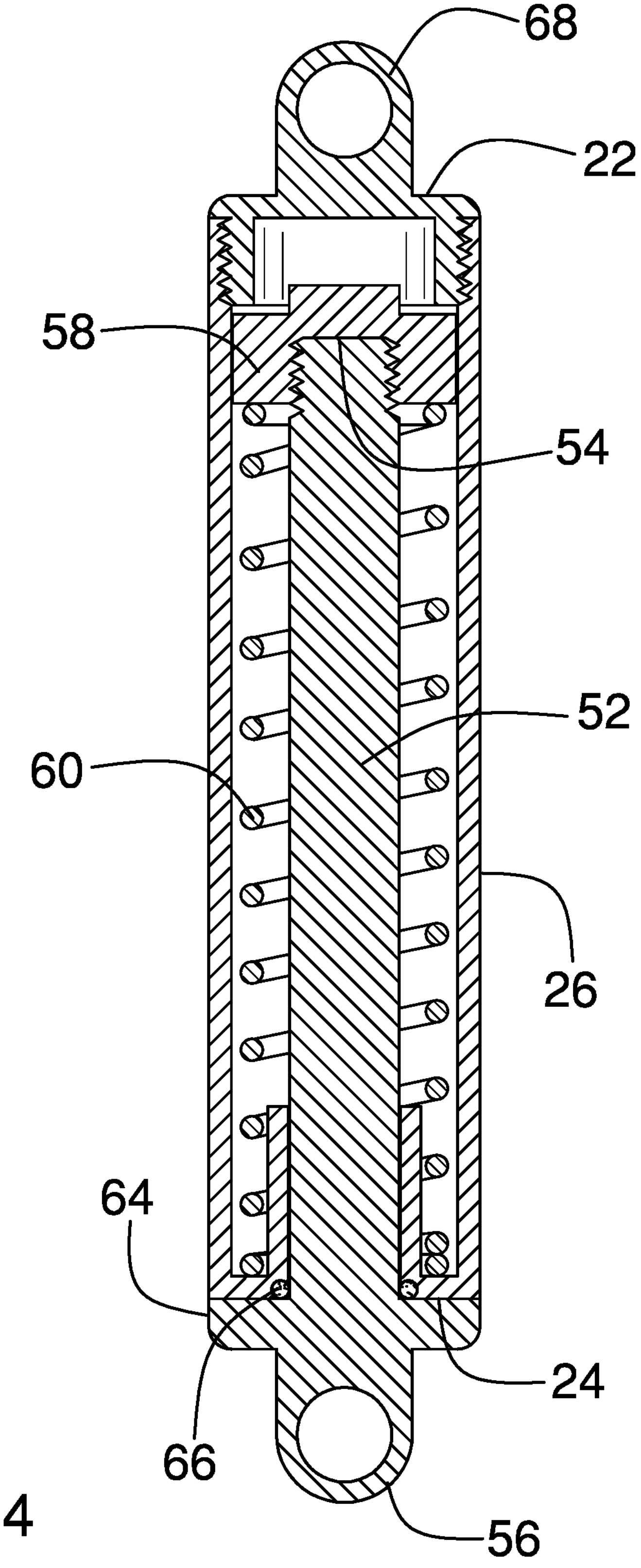
FIG. 4 is a cross-sectional view of an embodiment of the disclosure taken along line 4-4 of FIG. 1.
Figure 5:
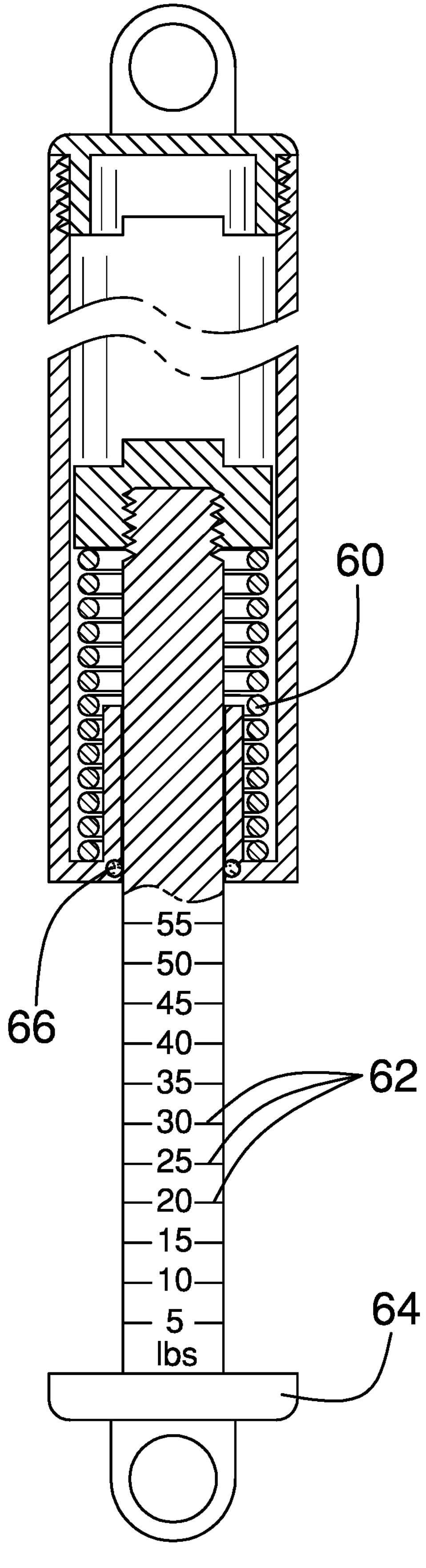
FIG. 5 is a broken side view of an embodiment of the disclosure.
Figure 6:
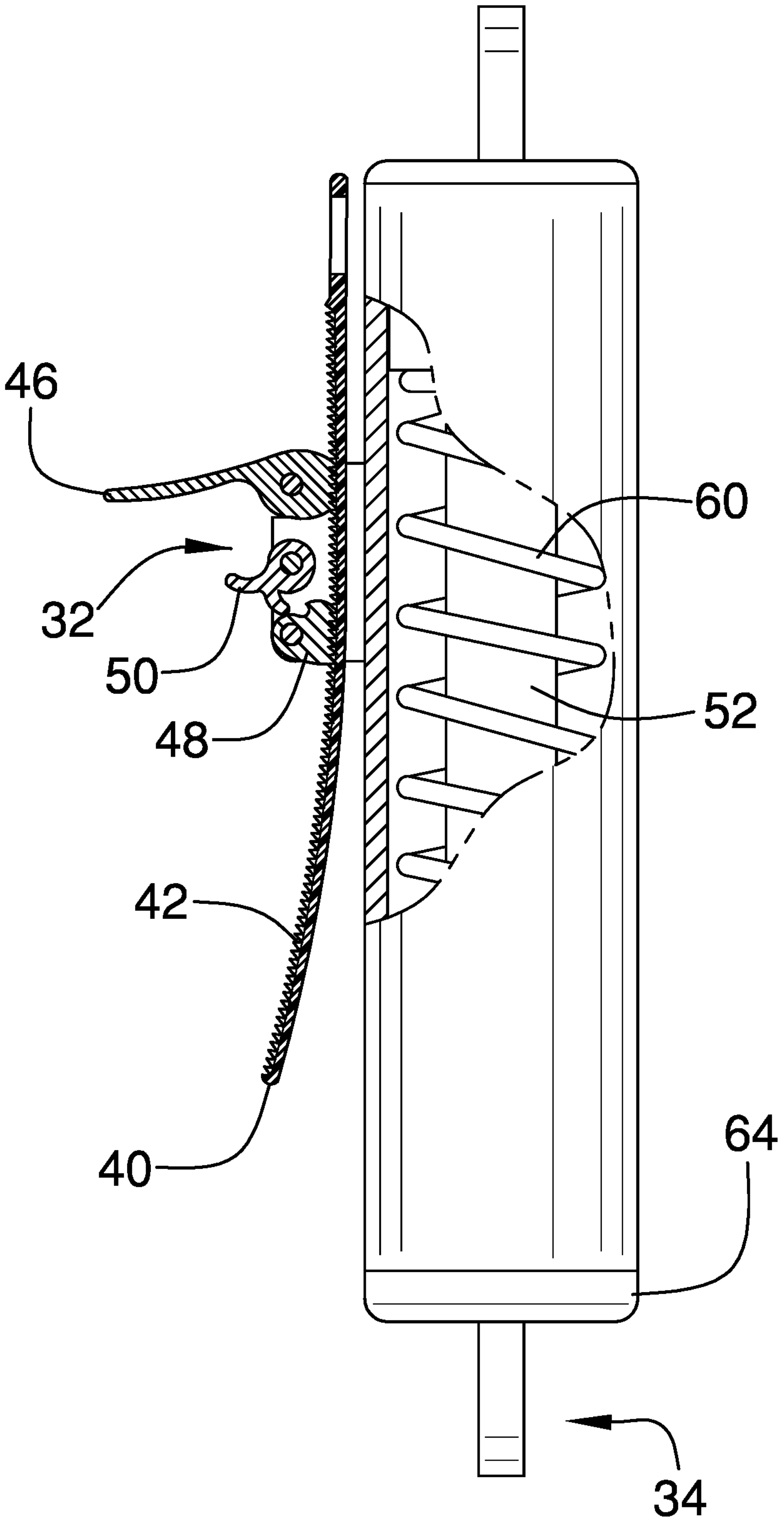
FIG. 6 is a broken front view of an embodiment of the disclosure.

The biasing member 38 comprises a compression spring 60 wherein the rod 52 extends through the spring 60. The compression spring 60 extends between and abuts the head 58 and an interior surface of the second end 24 of the housing 20 to bias the head 58 away from the second end 24. Thus, as the head 58 moves toward the second end 24, additional force is exerted by the spring 60 on the head 58. The increments of force may be measured, typically in pounds or kilograms, and that measurement may be displayed as indicia 62 along an exterior surface of the rod 52 as shown in FIG. 2. This will provide feedback to care providers as to the amount of force being pulled by the traction system 12 on a patient's leg 14. Should the measurement need to be calibrated, the first end 22 of the housing 20 is removed and the head 58 is rotated to adjust its position on the rod 52. A stop 64 on the rod 52 may be utilized to prevent the rod 52 from extending fully into the housing 20. A gasket 66 or seal may be mounted in the housing 20 and extend around and abut the rod 52 to prevent any materials, particularly liquids, from traveling into the housing 20.

It is well understood that alternate embodiments of the biasing member 38 may be utilized. For example, a tension spring or elastic band may be secured to the first end 22 of the housing and the internal end 54 of the rod 52 to pull the rod toward the first end 22. The head 58 may consist of a piston which compresses air or fluid within the housing 20 and in which case the urging assembly 32 may include a pump. However, springs or elastic bands are typically favored for affordability, easy of use and mechanical stability.

A receiver 68 configured for engaging a hook may be attached to the first end 22 of the housing 20. The receiver 68 may include a closed loop, hook, openable closed loop or any other structure used for coupling the housing 12 to a tether in secure manner. Typically a carabiner engageable receiver will be utilized for ease of use.

Figure 7:
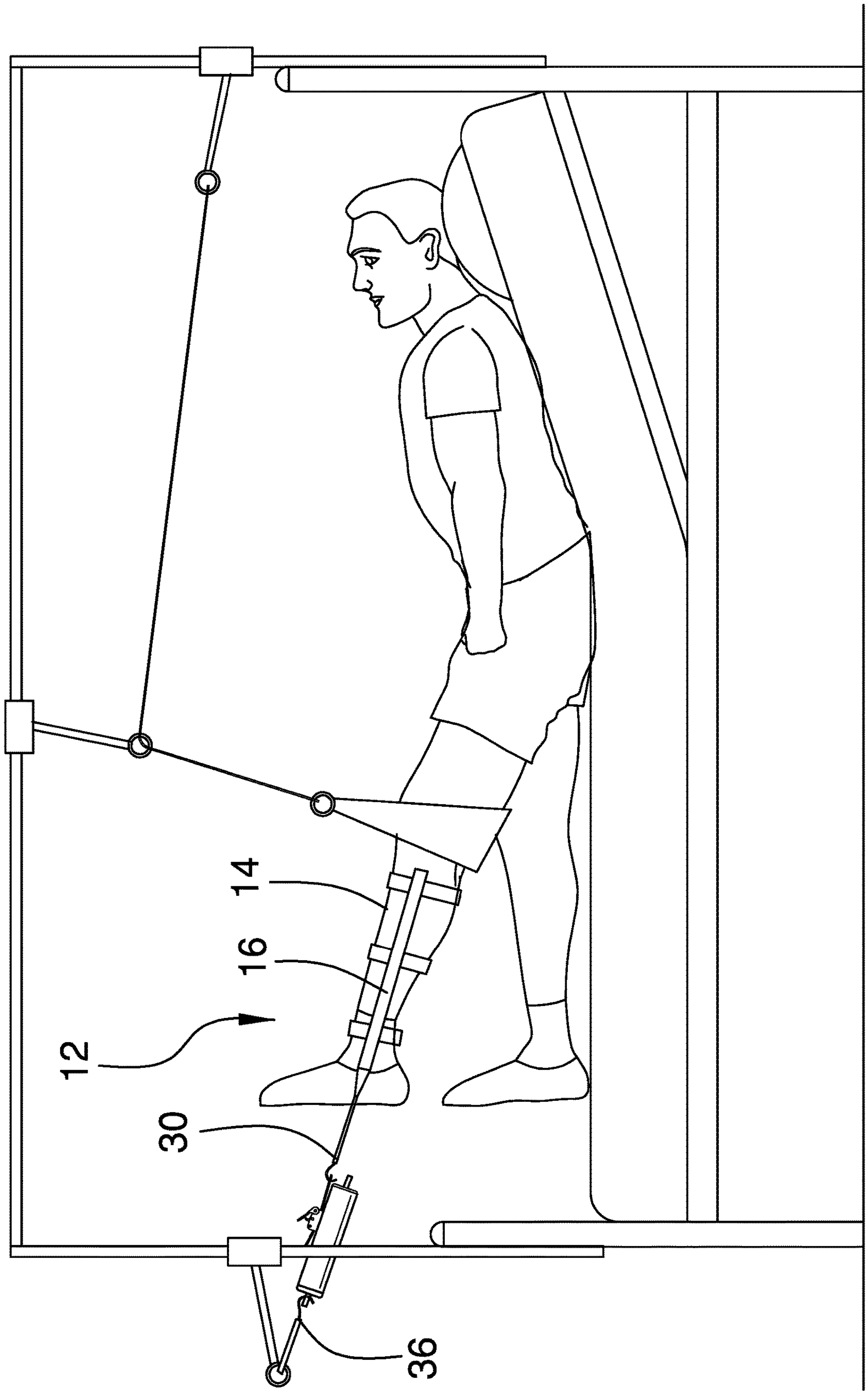
FIG. 7 is a side in-use view of an embodiment of the disclosure.
Figure 8:
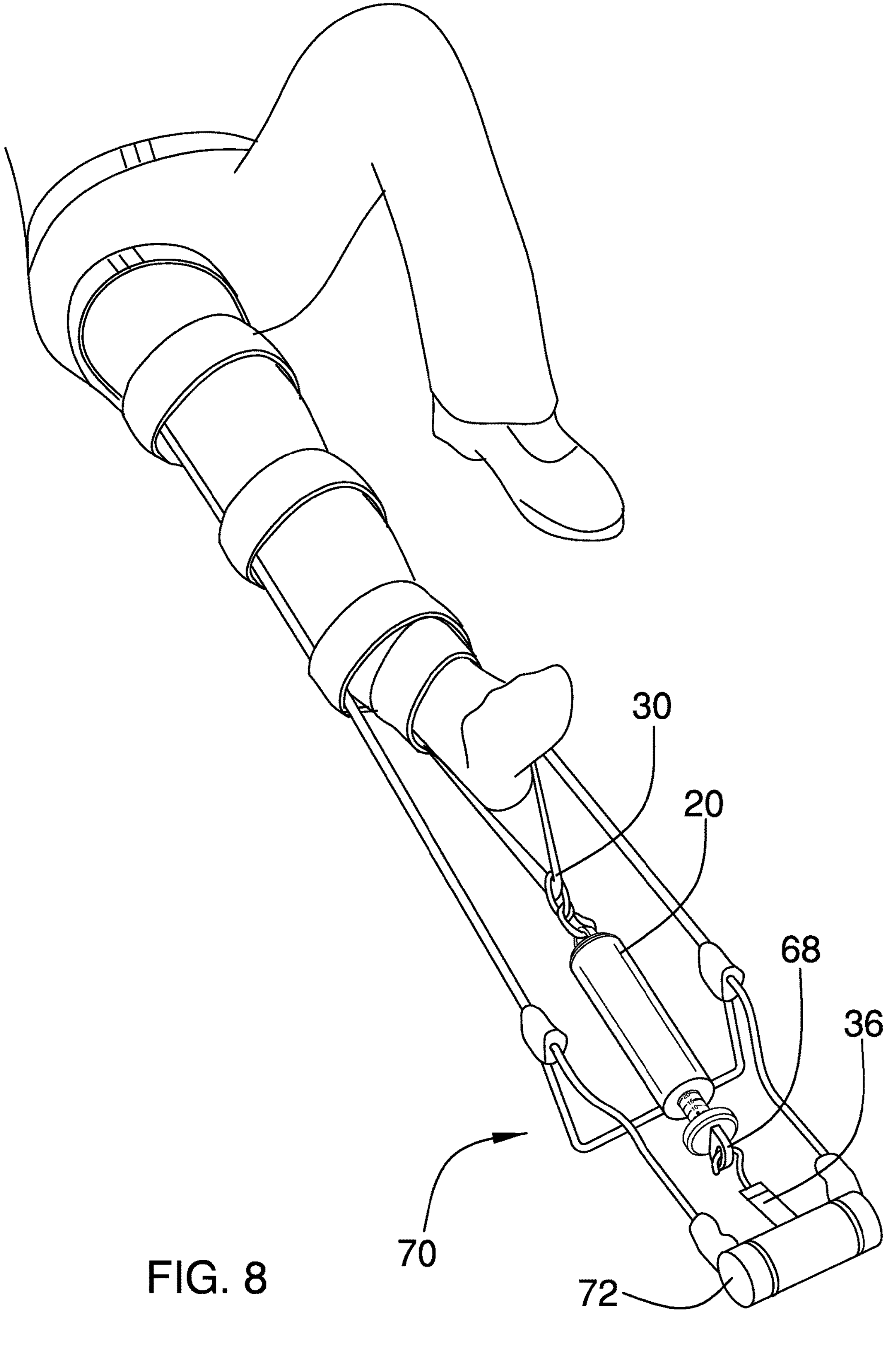
FIG. 8 is an in-use view of an embodiment of the disclosure.
Figure 9:
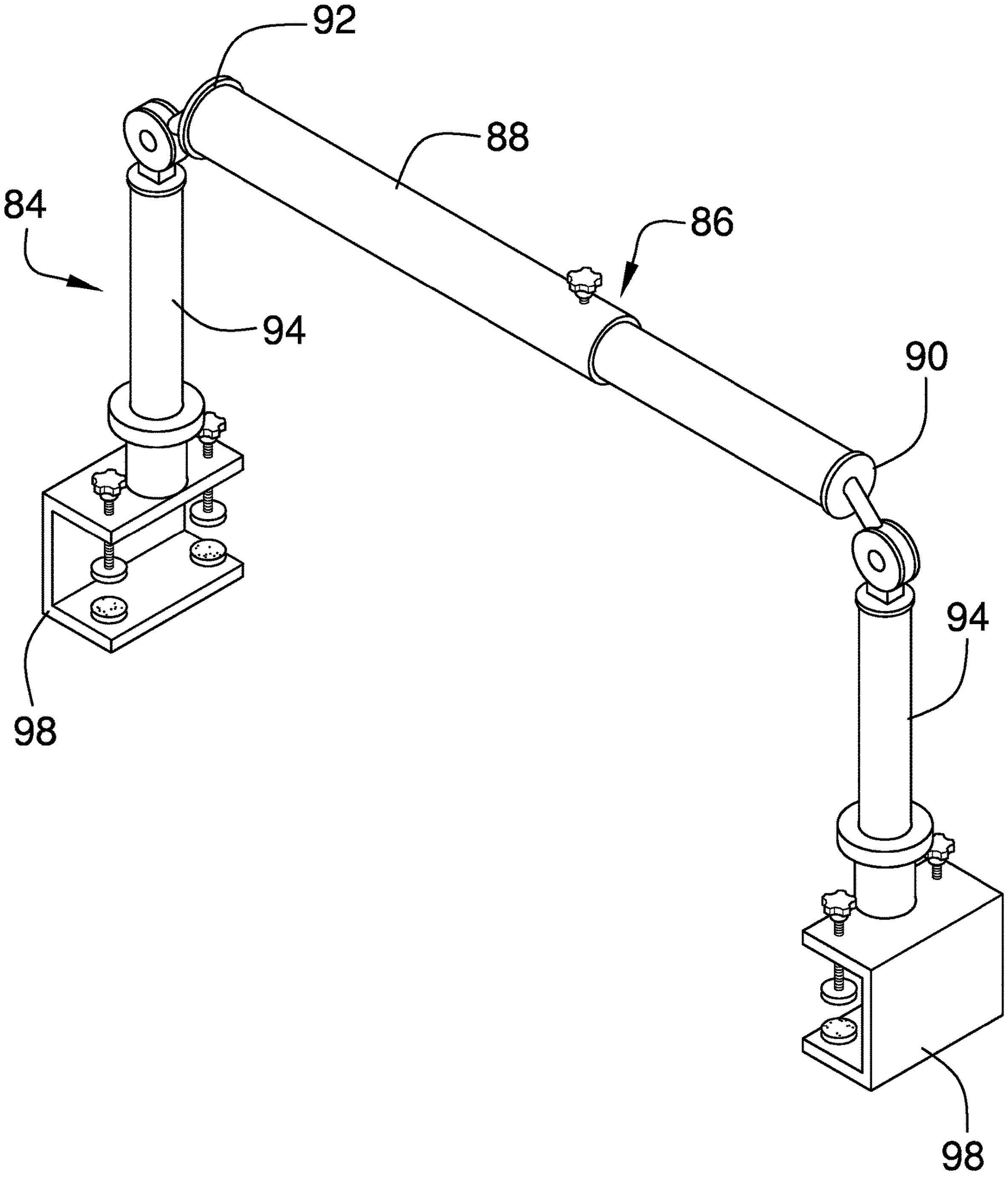
FIG. 9 is a front isometric view of a mount of an embodiment of the disclosure.

In use, the apparatus 10 is placed within a traction system 12, such as shown in FIGS. 7 and 8, to measure the force of traction being exerted on a patient's leg 14 and to easily adjust and monitor the amount of force being used. While this has been done with pulley's and weights in the past, the use of weights does not allow for easy transfer from a traction bed to another bed or an imaging table, such as to obtain an MRI, for instance, nor can weights be used in the field or on ambulances. As can be seen in FIG. 7, the apparatus 10 extends between the first tether 30 secured to the traction sling 16 or other point where the traction is to be applied including splints and pins. The second tether 36 is attached to a fixed point such as a bed or an article attached to the bed. The caregiver utilizes the urging assembly 32 against the biasing member 38 to create greater amounts of tension until the force being exerted by the biasing member 38 is at a selected level. Should the person need to move to another bed or imaging table, the attachment point 34 can be secured to a fixed-point relative to the other bed or imaging table to ensure that the amount of traction being applied remains constant.

In the field and as shown in FIG. 8, such as after a vehicle accident where a traumatic injury has occurred to the femur, the apparatus 10 can be used with a HARE splint 70 utilizing the receiver 68 and the attachment point 34 with the conventional hooks/carabiners often used with the HARE unit 70. The apparatus 10 ensures that the correct amount of tension is applied within the field while facilitating movement of the patient. A version of the apparatus 10 used with the HARE unit 70 might not include an anchor point 28 or urging assembly 32 since such an embodiment will instead attach the first tether 30 to the receiver 68 and utilize the ratchet mechanism 72 of the HARE unit 70, secured directly the attachment point 34, to function as the urging assembly 32 within the traction system 12.

To facilitate usage, the apparatus 10 may be utilized within a system 80 as shown in FIGS. 9-12. When a patient requires imaging, such as on an imaging bed 82 for an MRI, CAT scan, or other similar actions, there is a lack of an attachment point for the apparatus 10. To that end the system 10 includes a mount 84 that is attached to the imaging bed 82. The mount 84 includes a connection point 86, or location, attachable to the traction assembly, i.e. apparatus 10, such that the traction assembly 10 extends between and is coupled to the mount 84 and the person's leg 14. The mount 84, typically, will be removably attached to the imaging bed 82.

Figure 10:
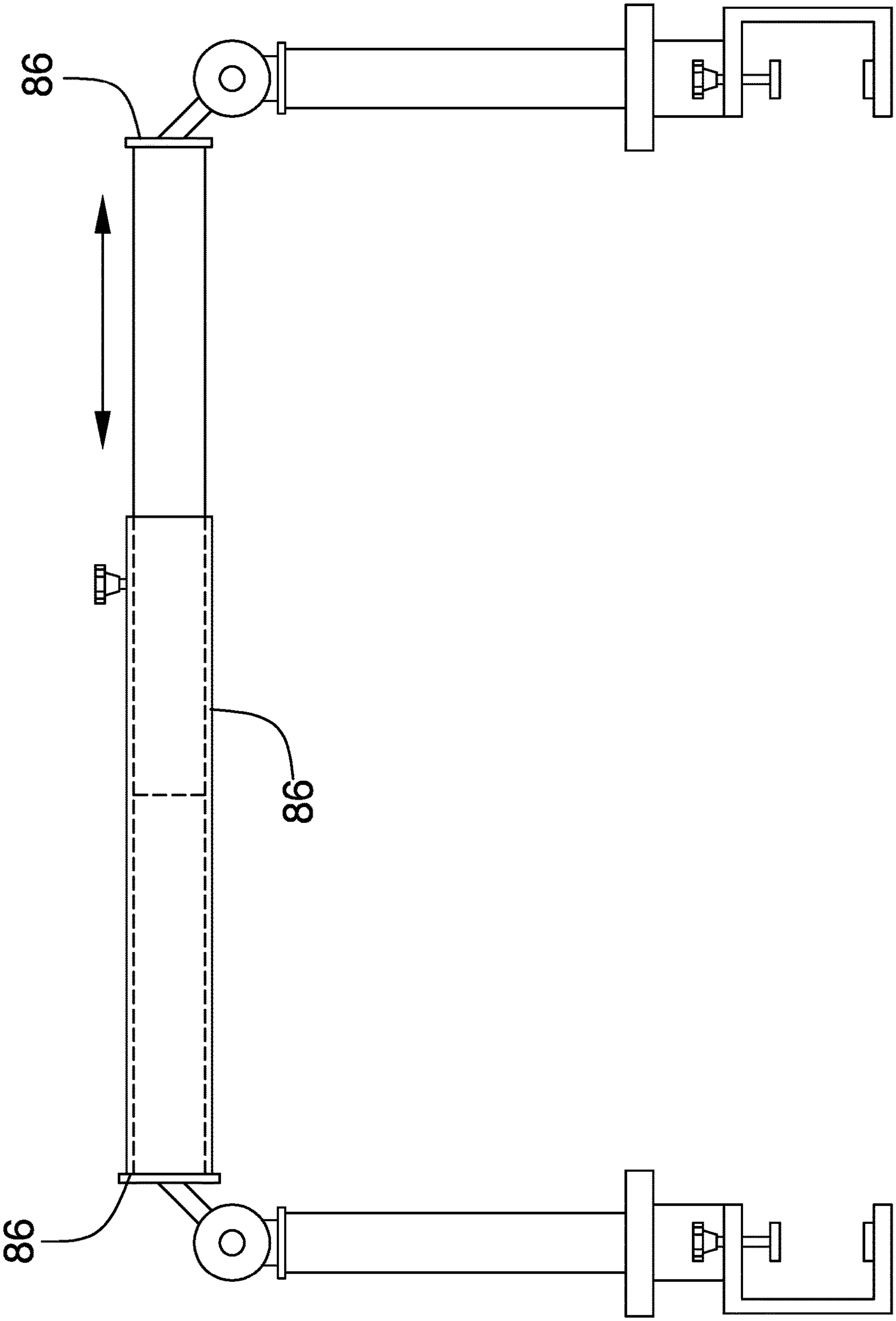
FIG. 10 is a front view of the mount an embodiment of the disclosure.
Figure 11:
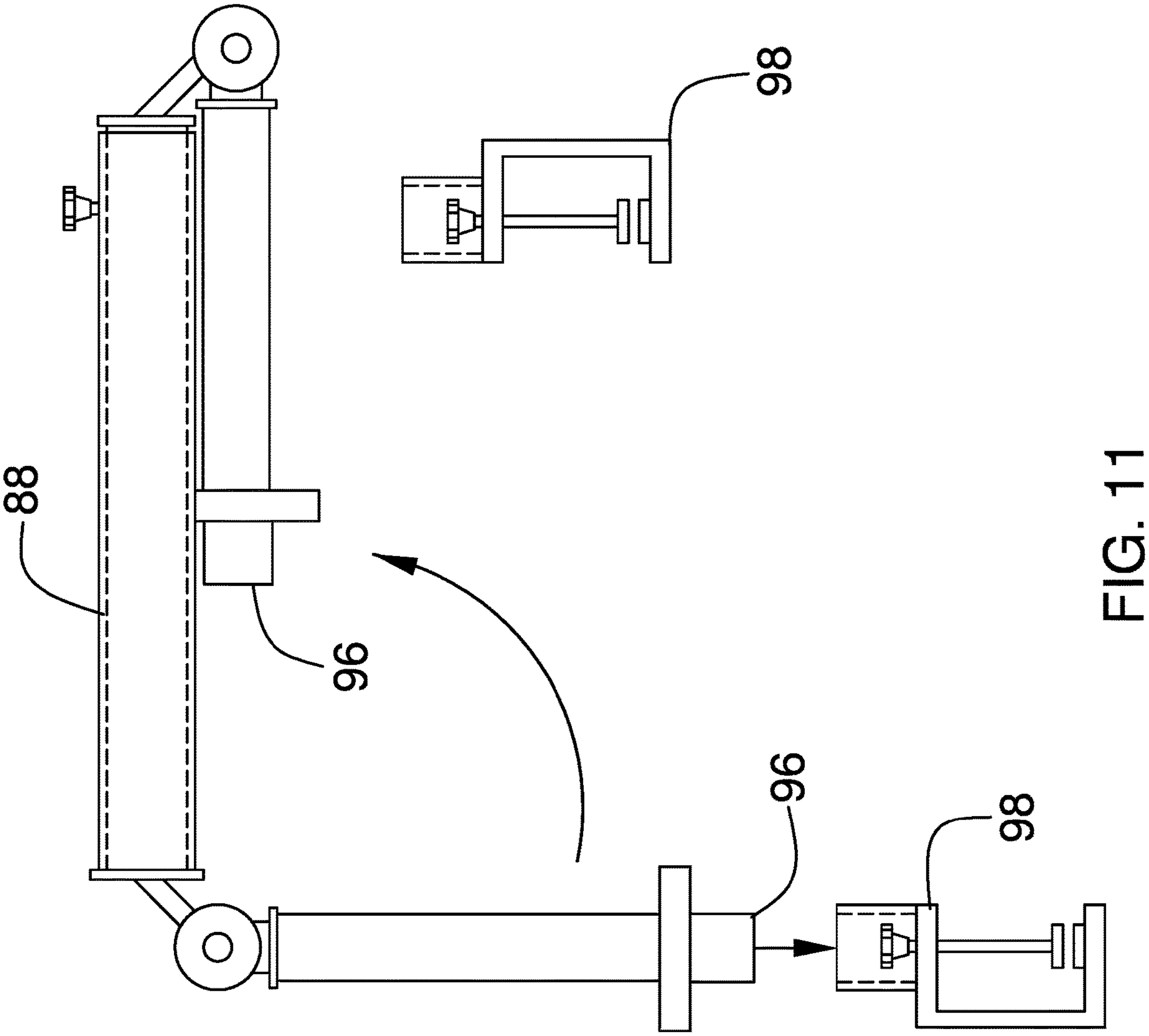
FIG. 11 is a front in-use view of the mount of an embodiment of the disclosure.
Figure 12:
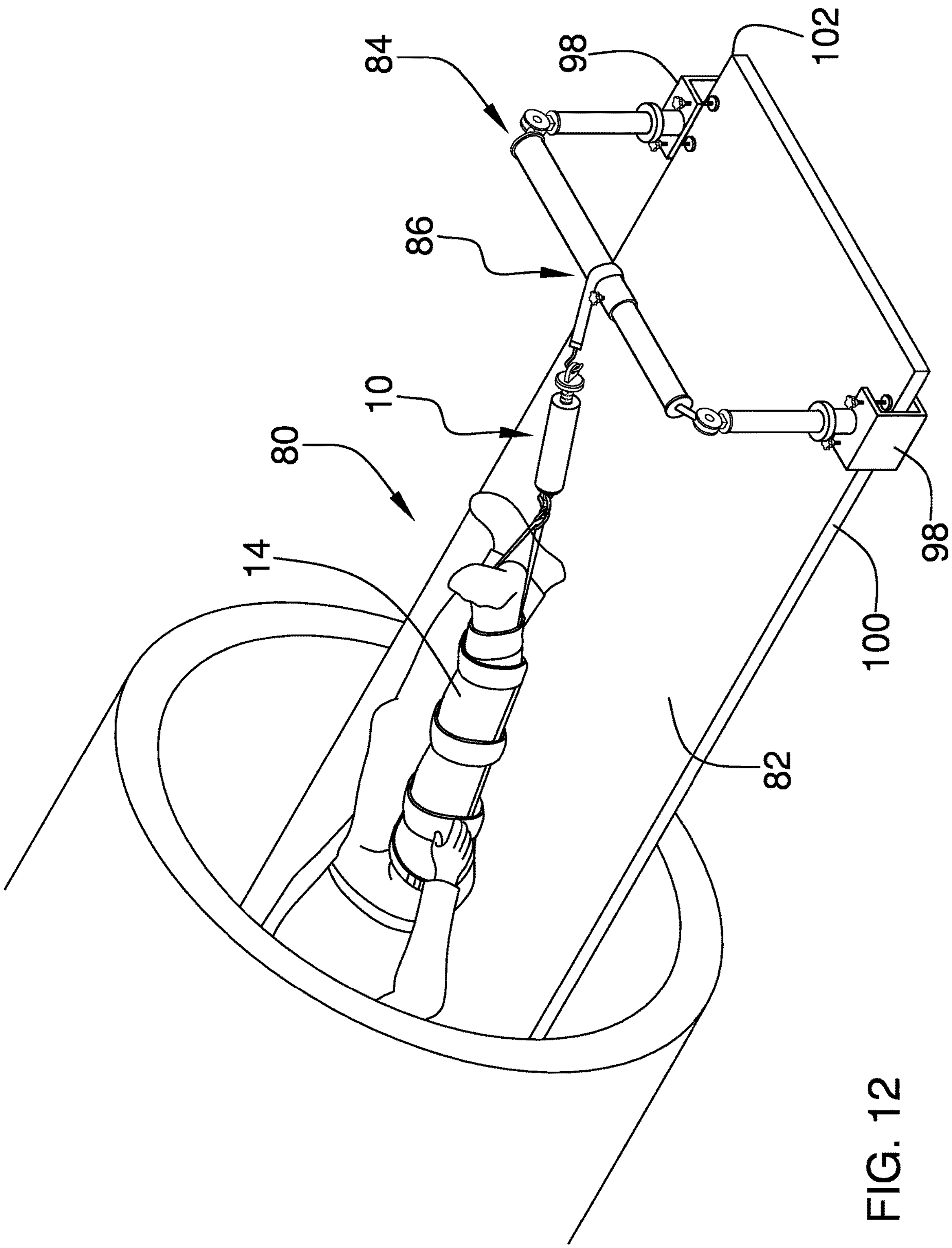
FIG. 12 is an isometric rear in-use view of the mount of an embodiment of the disclosure.

More particularly, the mount 84 includes a central member 88 having a first end 90 and a second end 92. The central member 88 forms the connection point 86 for connection to the traction assembly 10. The central member 88 may having an elongated tubular shape, which may be cylindrical, as shown and the connection point 86 may be located anywhere upon its length. Alternatively, or additionally, hooks or other attachment facilitating structure may be placed on the central member 88 for engagement with the first 30 or second 36 tethers depending on how the apparatus 10 is orientated and in a similar manner as with the traction bed shown in FIG. 7. The central member 88 may be telescopic as shown in FIG. 10 and have a length that is movable from about 12 inches to 30 inches depending on the length of sections comprising the central member 88.

A pair of arms 94 is attached to the central member 88. The arms 94 extend downwardly from the central member 88 and each has a distal end 96 with respect to the central member 88. The arms 94 each have a height typically from 4 inches to 24 inches. Though not required, the arms 94 may be pivotally coupled to the central member 88 for storage purposes. It should also be understood that the central member 88 may have an arcuate shape whereupon the arms 94 may be shortened or removed completely.

A pair of brackets 98 is provided and each of the distal ends 96 has one of the brackets 98 attached thereto. The brackets 98 may be removably attached or permanently attached to a respective one of the arm 94. One of the brackets 98 releasably engages a first lateral edge 100 of the imaging table 82 and one of the brackets 98 releasably engages a second lateral edge 102 of the imaging table 82 such that the central member 88 extends over a top surface of the imaging table 82. The brackets 98 may comprise each comprise a clamp or vise type bracket that is releasably and frictionally engaged with the imaging table 82. However, any structure capable of firmly gripping the imaging table 82 may be used as the bracket 98.

As stated above, the apparatus 10 and mount 84 allows a person to move from a traction bed to the imaging table 82 while keeping the person's leg 14 in traction. This is useful not only for the comfort of the patient, but allows the imaging equipment to be utilized while the leg is in traction to provide better viewing of the position of and damage to the person's bones and connective tissues. The mount 84, as well as the apparatus 10, may be comprised out of non-magnetically active materials to reduce concerns of their usage near strong magnetic fields.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An adjustable traction tensioning system configured to select a desired amount of traction to be applied to an extremity of a person, the system including:

a traction assembly configured for releasable engagement with a leg of a person to apply traction to the leg, the traction assembly including:

a housing having a first end, a second end and a perimeter wall extending between the first and second ends;

an anchor point being mounted to the housing and being configured to be attached to a first tether being in-line with a traction system and extending away from the housing in a first direction;

an urging assembly being engaged with the anchor point, the urging assembly being tension actuated to urge the anchor point toward the second end and releasably actuated to allow the anchor point to move toward the first end;

an attachment point being mounted to the housing and being configured to be attached to a second tether being in-line with the traction system and extending away from the housing in a second direction, the attachment point being movable in the first and second directions relative to the housing;

a biasing member being engaged with the attachment point and biasing the attachment point in the first direction; and a mount being attached to an imaging bed, the mount including a connection point attached to the traction assembly such that the traction assembly extends between and is configured to be coupled to the mount and the leg of the person, the mount being removably attached to the imaging bed;

wherein the mount comprises:

a central member having a first end and a second end, the central member forming the connection point for connection to the traction assembly;

a pair of arms being attached to the central member and extending downwardly away from the central member, each of the arms having a distal end with respect to the central member;

a pair of brackets, each of the distal ends having one of the brackets attached thereto, one of the brackets releasably engaging a first lateral edge of the imaging bed and one of the brackets releasably engaging a second lateral edge of the imaging bed such that the central member extends over a top surface of the imaging bed; and the urging assembly being positioned on the perimeter wall of the housing, the urging assembly extending laterally outward from the perimeter wall of the housing, the urging assembly being positioned spaced from each of the first end of the housing and the second end of the housing, wherein the urging assembly includes:

a strap being attached to the anchor point, the anchor point being attached to the strap; and a ratchet mechanism being engaged with the strap, wherein the ratchet mechanism is tension actuated to pull the anchor point in the second direction.

2. The adjustable traction tensioning system according to claim 1, wherein the attachment point includes:

a rod slidably extending through the second end of the housing, the rod having an internal end positioned within the housing and an external end positioned external of the housing, wherein the second tether is attachable to the rod adjacent to the external end;

a head being mounted on the internal end of the rod; and the biasing member comprising a compression spring, the rod extending through the spring, the rod abutting the head and an interior surface of the second end of the housing to bias the head away from the second end.

3. The adjustable traction tensioning system according to claim 2, wherein the rod threadably receives the internal end, the first end of the housing being removably attached to the perimeter wall to facilitate access to the head, wherein a position of the head on the rod is adjustable.

4. The adjustable traction tensioning system according to claim 3, wherein the anchor point includes a closed loop, a hook, or an openable loop for engagement with the first tether, and wherein the attachment point includes a closed loop, a hook, or an openable loop for engagement with the second tether.

5. The adjustable traction tensioning system according to claim 1, wherein the central member is telescopic and having an adjustable length.

6. The adjustable traction tensioning system according to claim 5, wherein each of the arms has a height being between 4 inches and 24 inches.

7. The adjustable traction tensioning system according to claim 1, wherein the brackets each comprise a clamp being releasably and frictionally engaged with the imaging table bed.

* * * * *